United States Patent
Kshirsagar et al.

(10) Patent No.: US 9,526,684 B2
(45) Date of Patent: Dec. 27, 2016

(54) ISOTROPIC, FLOWABLE, SKIN PH AQUEOUS CLEANSING COMPOSITIONS COMPRISING N-ACYL GLYCINATES AS PRIMARY SURFACTANTS

(71) Applicant: Galaxy Surfactant, Ltd., Maharashtra (IN)

(72) Inventors: Pooja Vaidya Kshirsagar, Nagpur (IN); Nirmal Koshti, Piscataway, NJ (US); Pramod Bipracharan Sabat, Dombivli (IN); Bhagyesh Jagannath Sawant, Maharashtra (IN)

(73) Assignee: Galaxy Surfactant, Ltd. (IN)

( * ) Notice: Subject to any disclaimer, the term of this patent is extended or adjusted under 35 U.S.C. 154(b) by 0 days.

(21) Appl. No.: 14/832,322

(22) Filed: Aug. 21, 2015

(65) Prior Publication Data
US 2016/0228343 A1    Aug. 11, 2016

(30) Foreign Application Priority Data
Aug. 25, 2014   (IN) .......................... 2715/MUM/2014

(51) Int. Cl.
| | | |
|---|---|---|
| A61K 8/46 | (2006.01) | |
| A61K 8/44 | (2006.01) | |
| A61Q 19/10 | (2006.01) | |
| A61Q 19/00 | (2006.01) | |
| A61Q 5/02 | (2006.01) | |

(52) U.S. Cl.
CPC .............. *A61K 8/466* (2013.01); *A61K 8/442* (2013.01); *A61Q 5/02* (2013.01); *A61Q 19/007* (2013.01); *A61Q 19/10* (2013.01); *A61K 2800/80* (2013.01)

(58) Field of Classification Search
None
See application file for complete search history.

(56) References Cited

U.S. PATENT DOCUMENTS

| | | |
|---|---|---|
| 5,415,810 A | 5/1995 | Lee et al. |
| 5,925,603 A | 7/1999 | D'Angelo |
| 7,655,607 B2 | 2/2010 | Tsaur et al. |
| 7,674,759 B2 | 3/2010 | Tsaur |
| 7,879,780 B2 | 2/2011 | Tsaur |
| 8,105,994 B2 | 1/2012 | Tsaur et al. |

(Continued)

FOREIGN PATENT DOCUMENTS

| | | |
|---|---|---|
| WO | 2014030038 A1 | 2/2014 |
| WO | 2014181342 A1 | 11/2014 |

OTHER PUBLICATIONS

Ananthapadmanabhan KP, Moore DJ, Subramanyan K., et. al., "Cleansing without compromise: the impact of cleansers on the skin barrier and the technology of mild cleansing", Dermatol Ther 2004; 17 Suppl 1:16-25.

(Continued)

*Primary Examiner* — Aradhana Sasan
(74) *Attorney, Agent, or Firm* — Lerner, David, Littenberg, Krumholz & Mentlik, LLP

(57) ABSTRACT

Disclosed is an aqueous cleansing composition comprising N-acyl glycinates as primary surfactants wherein the said cleansing compositions are isotropic and flowable at skin pH. The aqueous cleansing compositions are isotropic and flowable at temperature 25° C. Also disclosed is the use of these aqueous cleansing compositions in preparing isotropic aqueous personal skin and hair cleansing formulations such as body wash, shower gels, shampoos, and other such products.

9 Claims, 6 Drawing Sheets

(56) References Cited

U.S. PATENT DOCUMENTS

| | | | |
|---|---|---|---|
| 8,124,574 | B2 | 2/2012 | Tsaur et al. |
| 8,263,538 | B2 | 9/2012 | Tsaur et al. |
| 8,268,767 | B2 | 9/2012 | Tsaur et al. |
| 2009/0062406 | A1 | 3/2009 | Loeffler |
| 2012/0046210 | A1 | 2/2012 | Patel et al. |
| 2013/0189212 | A1 | 7/2013 | Jawale et al. |

OTHER PUBLICATIONS

E. Kim et. al., "The alkaline pHadapted skin barrier is disrupted severely by SLS-induced irritation", International Journal of Cosmetic Science, Aug. 2009 ; 31(4):263-269.

Keller and Heckman LLP, "Assessment Plan for Fatty acids, coco, sulfoethyl esters, sodium salts (sodium cocoylisethionate)", Nov. 2006.

Rippke F. et. al., "Stratum corneum pH in atopic dermatitis: impact on skin barrier function and colonization with *Staphylococcus aureus*", The American Journal of Clinical Dermatology, 2004; 5(4) : 217-223.

Saba M. Ali and Gil Yosipovitch, "Skin pH: From Basic Science to Basic Skin Care", Department of Dermatology, Wake Forest University Baptist Medical Center, Winston-Salem 2013 ; 93 : 261-267.

Figure 1: During Application and Washing
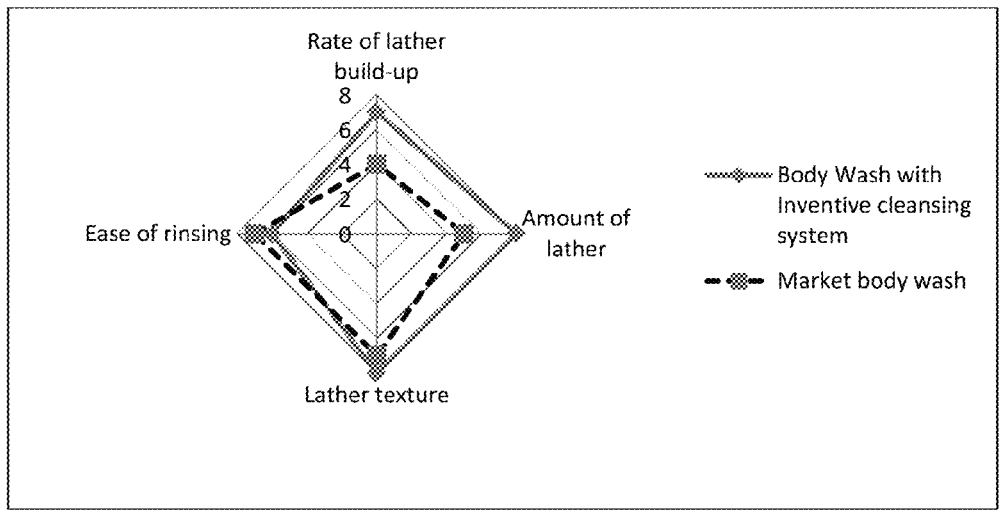
Figure 2: Immediately After Drying
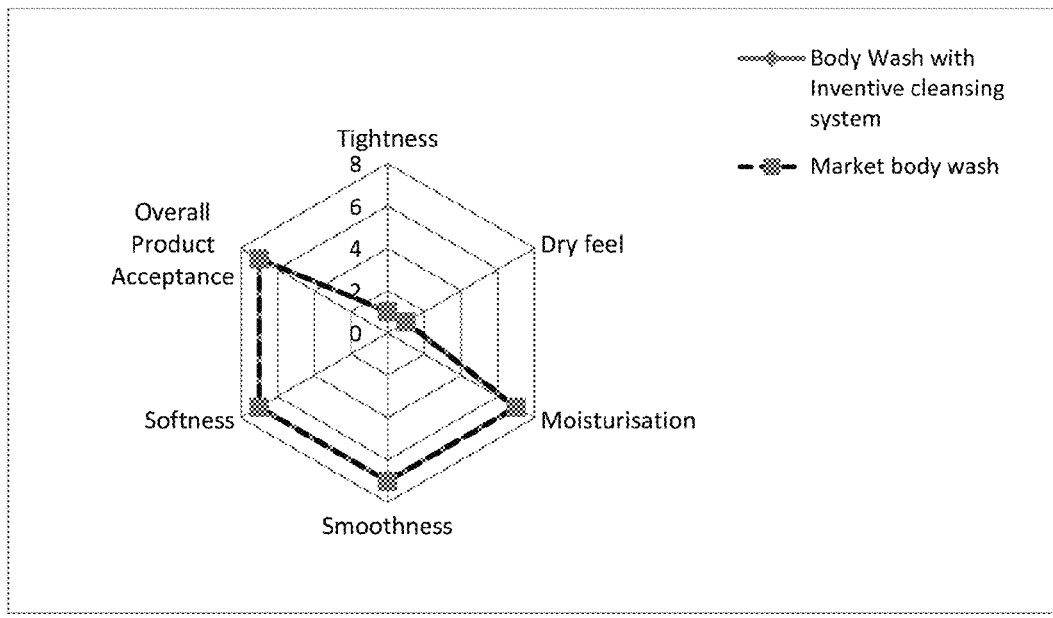

Figure 3: After 10 minutes of Drying
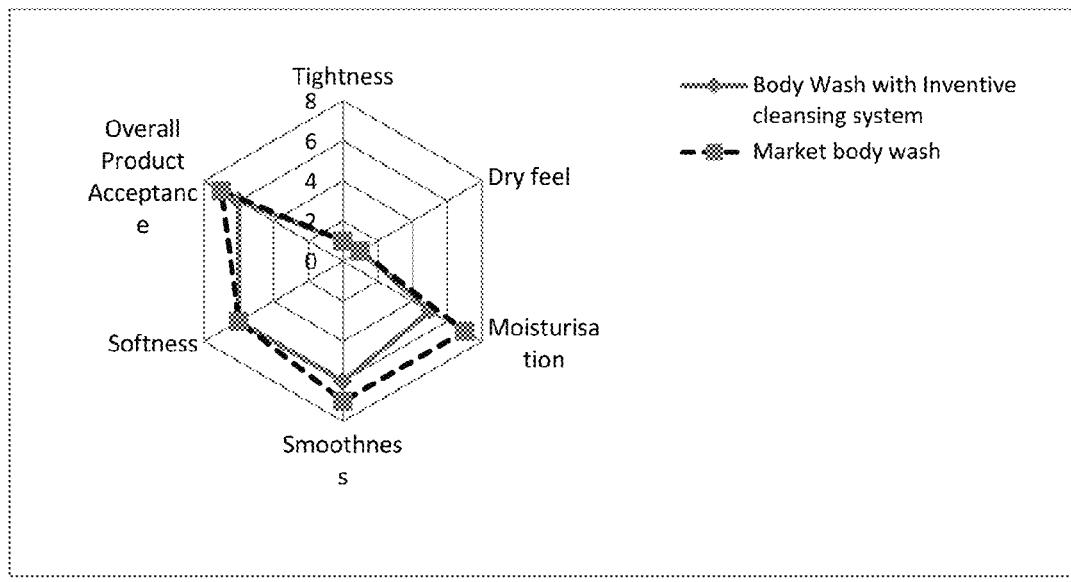

ISOTROPIC, FLOWABLE, SKIN PH AQUEOUS CLEANSING COMPOSITIONS COMPRISING N-ACYL GLYCINATES AS PRIMARY SURFACTANTS

CROSS-REFERENCE TO RELATED APPLICATION(S)

The present application claims priority from India Application No. 2715/MUM/2014 filed Aug. 25, 2014, the disclosure of which is hereby incorporated herein by reference.

FIELD OF INVENTION

The present invention relates to novel aqueous cleansing composition comprising N-acyl glycinates as primary surfactants wherein the said cleansing compositions are isotropic and flowable at pH less than 7, more specifically at skin pH. The aqueous cleansing compositions are isotropic and flowable at temperature 25° C. The present invention also relates to the use of these aqueous cleansing compositions in preparing isotropic aqueous personal skin and hair cleansing formulations such as body wash, shower gels, shampoos, and other.

BACKGROUND OF THE INVENTION

The origins of personal cleanliness date back to prehistoric times. Fatty alkyl carboxylate, commonly known as soap, is the first prototypical surfactant used for personal cleansing as early as 2800 B.C., followed by synthetic anionic surfactants such as alkyl benzene sulfonates and fatty alcohol sulfates developed in 1900s. However, the drawback of these anionic surfactants is that by their very nature they are harsh, they remove excess of natural oil i.e. sebum from hair and skin, thus causing damage to skin and hair lipids and proteins, leading to after-wash tightness, dryness, barrier damage, irritation, and itching. Therefore, the surfactant manufacturing industry started its first extensive research in developing "MILD" surfactants. As a first step towards this research, ethoxylated anionic surfactants such as sodium lauryl ether sulfates, nonionic surfactants such as fatty alcohol ethoxylates, and amphoteric surfactants such as betaines and amphoacetates were developed. Although, amphoteric and nonionic surfactants are mild surfactants but are not as good cleansers and foamers as anionic surfactants, whereas ethoxylated anionic surfactants although are good cleansers but not anymore remain a desirable surfactant because of its impurity profile which contains 1,4-dioxane that is toxic. Thus there were mild surfactants but not good cleansers, whereas there were good cleansers but were not mild.

SUMMARY OF THE INVENTION

It is an objective of the present invention to develop an isotropic cleansing composition to solubilize N-acyl glycinates in aqueous form at skin pH It is another objective of the present invention to create isotropic cleansing compositions comprising N-acyl glycinate as a primary surfactant i.e. it is present in quantity equal or higher than the other surfactants of the composition.

It is yet another objective of the present invention to develop an aqueous cleansing composition to solubilize N-acyl glycinates wherein the said aqueous cleansing composition is isotropic and flowable at skin pH.

It is also an objective of the present invention to combine N-acyl glycinates and O-acyl isethionates in aqueous form at skin pH.

It is also an objective of the present invention to prepare the aqueous cleansing composition without employing any non-surfactant ingredients.

It is also an objective of the present invention to prepare aqueous cleansing composition having skin pH which remains isotropic and flowable at temperature 25° C.

The present invention provides novel aqueous cleansing compositions to solubilize N-acyl glycinate as a primary surfactant wherein the said aqueous cleansing compositions have skin pH and remain isotropic and flowable at ambient temperature i.e. 25° C.

Accordingly, the present invention relates to aqueous cleansing compositions comprising:

An aqueous blend of N-acyl glycinates of Formula I and O-acyl isethionates of Formula II;

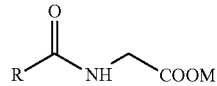

Formula I

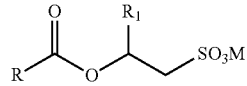

Formula II wherein,

R is selected from $C_5$ to $C_{22}$ alkyl group, saturated or unsaturated, $R_1$ is selected from H or methyl, and M is a cation selected from $Li^+$, $Na^+$, $K^+$, $NH4^+$ or a quaternary ammonium cation derived from tertiary amines;

said aqueous blend is prepared by the process comprising steps of

A) reacting more than one equivalence of fatty acid chloride with alkali metal or ammonium salts of hydroxyalkyl sulphonates to prepare compounds of Formula II, B) reacting the product of step (A) (containing the remainder fatty acid chloride) with glycine in the presence of a base under typical aqueous Schotten Baumann reaction conditions to form compounds of Formula I.

wherein the weight ratio of N-acyl glycinates of Formula I to O-acyl isethionates of Formula II is in range of 1.0:1.0 to 10.0:1.0, and (ii) A solubilizing surfactant wherein the weight ratio of (i):(ii) is from 1.0:0.1 to 1.0:1.0, and wherein the aqueous cleansing composition is isotropic and flowable at skin pH i.e. pH 5.0 to 6.0.

The novel aqueous cleansing composition of the present invention acts as a vehicle to solubilize N-acyl glycinates as primary surfactants. These cleansing compositions have pH 5.0 to 6.0 (skin pH) and still remain isotropic and flowable at temperature 25° C.

The novel aqueous cleansing composition of the present invention is prepared by preparing an aqueous blend of N-acyl glycinate of Formula I and O-acyl isethionate of Formula II; and adding at least one solubilizing surfactant to the said aqueous blend The present invention also relates to aqueous personal cleansing formulations such as body wash, face wash, shower gels, shampoos, etc. comprising the said novel aqueous cleansing compositions.

BRIEF DESCRIPTION OF DRAWINGS

In the drawings, wherein similar reference characters denote similar elements throughout the several views:

FIG. 1 shows a graphical representation of user sensorial properties of the inventive composition during application and washing;

FIG. 2 shows a graphical representation of user sensorial properties of the inventive composition immediately after drying; and FIG. 3 shows a graphical representation of user sensorial properties of the inventive composition after 10 minutes of drying.

DETAILED DESCRIPTION

The surfactant industry continued their expedition for surfactants having multifunctional properties i.e. along with cleansing, they should also provide other desired benefiting attributes such as mildness, skin and hair sensory to the formulations. It resulted into development of a different category of surfactants which could have multiple properties. This new category of surfactants is amino acid-based surfactants.

N-acyl glycinate salts are one of the fundamental amino acid-based surfactants introduced as an essential surfactant by the formulators in their niche products due to its unique properties. N-acyl glycinate (salts) is an anionic surfactant having the general formula as

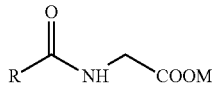

wherein R is selected from $C_5$ to $C_{22}$ alkyl group, saturated or unsaturated, and M is a cation selected from $Li^+$, $Na^+$, $K^+$, $NH4^+$ or a quaternary ammonium cation derived from tertiary amines.

Figure 4:
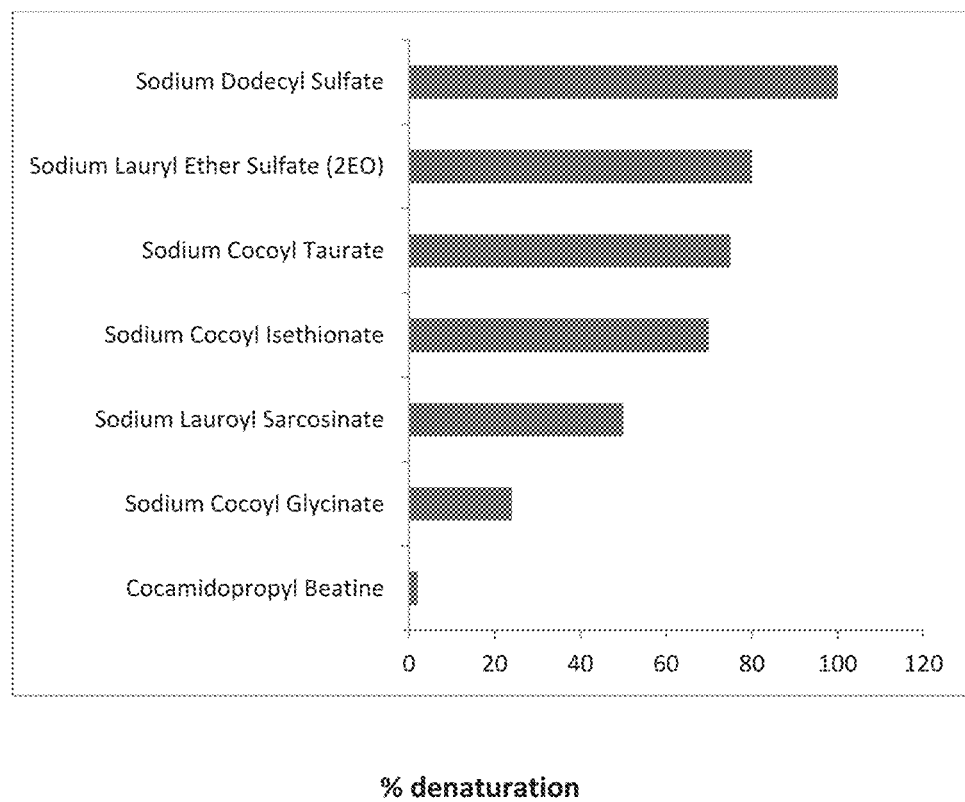
FIG. 4 illustrates testing results on various surfactants for mildness (% denaturation).

N-acyl glycinates are derived from natural coco fatty acid and the glycine. Glycine is one of the most abundant amino acids present in the structural proteins (collagen) of human skin and hair. Thus, being compatible to the skin and hair proteins, amino acid-based surfactants especially N-acyl glycinates protect the skin barrier (stratum corneum) function, which rapidly decreases due to loss in Natural Moisturizing Factor (NMF) during cleansing. N-acyl glycinates enhance and protect the intercellular lipids and thus smoothen the skin and hair. Moreover, glycine being the smallest of the naturally occurring amino acids; the charged head group on N-acyl glycinates is significantly smaller than many other surfactants. This small size facilitates production of smaller surfactant micelles and the generation of a creamy lather during use. Further, as N-acyl glycinates are prepared from natural occurring coco fatty acid and glycine, they are biodegradable too. It has been tested that no anionic surfactant other than sodium cocoyl glycinate is near to amphoteric surfactant (betaine) in terms of mildness. FIG. 4 is a graph showing the results of Red Blood Cells test done for mildness for various surfactants. Red Blood Cells test is a colorimetric test that correlates surfactant mildness to lack of disruption of the red blood cell membranes. A lower number of % denaturation equates to a milder surfactant.

Personal cleansers have an effect on skin condition and particularly the skin barrier (stratum corneum) in several ways. Many characteristics of a cleanser can be considered that affect skin barrier, but most important of these is its pH. Reports show that pH of formulations has a great impact on skin and hair. Therefore the goal of a formulator is to have cleansing composition that has pH that is compatible with skin. The range of the natural pH of the skin surface is reported broadly as from 4.0 to 6.0 and particularly as from 5.0 to 6.0 (Review Article on "Skin pH: From Basic Science to Basic Skin Care" by Saba M. Ali and Gil Yosipovitch Department of Dermatology, Wake Forest University Baptist Medical Center, Winston-Salem USA, Acta Derm Venereol 2013; 93: 261-267) and this so called Skin pH which indicates that the skin is in a healthy condition in terms of the biophysical parameters of barrier function, moisturization, and regulation of bacterial flora ("Stratum corneum pH in atopic dermatitis: impact on skin barrier function and colonization with *Staphylococcus aureus*" by Rippke F et. al, *The American Journal of Clinical Dermatology*, 2004; 5(4):217-23).

The high pH of cleansers can aggravate surfactant-induced dryness and irritation. The alkaline skin care products impair the skin barrier function wherein TEWL (transepidermal water loss) is increased significantly in comparison with acidic cleansing products. So, this implies that pH of personal cleansing products we use daily is very important for the skin barrier, homeostasis and sensitivity ("The alkaline pH-adapted skin barrier is disrupted severely by SLS-induced irritation" by E. Kim et. al., International Journal of Cosmetic Science, 2009 August; 31(4): 263-9.)

In addition, recent studies shown that high-pH solutions, even in the absence of surfactants, can increase stratum corneum swelling and alter lipid rigidity, which suggests that cleansers with a neutral or acidic pH are potentially less damaging to the skin ("Cleansing without compromise: the impact of cleansers on the skin barrier and the technology of mild cleansing." By Ananthapadmanabhan K P, Moore D J, Subramanyan K, et al., Dermatol Ther 2004; 17 Suppl 1:16-25) and hence pH of most of the mild cleansers is below pH 6, for example L'Oreal's EverPure® sulfate-free formulations have pH of about 5.8

The pH of the skin varies at different areas of the body. The feminine hygiene washes such as vaginal wash (e.g. VWash Plus) has pH between 3.5-4.5; as this area of the body has very low pH and therefore high pH cleansers are not acceptable for such applicable. Further, cleansing formulations for Babies need to have low pH of around 5.0-5.8. Since baby skin is very delicate and the skin barrier function is not developed fully in them, an extra care i.e. mildness, no tear, no dryness, and low pH is required. Shower gels are another segment of cleansers which is increasingly used and need those surfactants which can be incorporated to formulate low pH clear cleansers. Facial gels are yet another segment of personal care formulations which need to have mild surfactants. Facial skin is thin and delicate as compared to other area of the body and further facial gel/cleanser manufacturer has to be careful that such formulations do not impart any eye irritation.

Another major requirement of personal care industry is isotropic formulations. 'Isotropic' means 'clear and transparent'. Such formulations are aesthetically appealing wherein isotropicity is associated with attributes such as pureness, mildness, cleanliness, freshness, lightness and often possessing cooling properties. Some of the known brands which are isotropic are 'Neutrogena Oil Free Acne Wash Facial Cleanser', 'Neutrogena Visibly Clear Pore & Shine Daily Wash', 'Palmolive Men Revitalising Sport 2 in 1 Haut & Haar Duschgel and Shampoo', 'Right Guard Women brand (by Henkel)'. Further, 80% of baby care products are isotropic. Another benefit of a clear appearance, in combination with transparent packaging, is that the consumer is readily able to view and inspect the product.

Thus, the characteristics those keenly desired by consumers and the formulators to have in a personal cleansing formulation are:

Skin pH i.e. pH between 5.0 to 6.0
Isotropic in appearance;
Mild;
Provide good sensorial benefits;
No eye irritation;
Sulfate free;
Dioxane free; and
Cold processable.

As mentioned hereinbefore, N-acyl glycinates are one of the amino-acid based surfactants being presently used very demandingly in personal cleansers and gels. This is due to its function to protect skin barrier (stratum corneum) and hence providing mildness. Additionally it provides moisturisation. However, it is found that it is very difficult to formulate skin pH isotropic aqueous personal cleansers, comprising N-acyl glycinates, and this is because N-acyl glycinate salt gets converted into N-acyl glycine at acidic pH i.e. carboxylate form gets converted to carboxylic acid form which is water-insoluble. This insoluble fatty matter (carboxylic acid form) imparts haziness to the formulation. Therefore, aqueous personal care formulations comprising N-acyl glycinates are preferably made at alkaline pH to achieve and maintain the isotropy. However, there are still some cleansers and gels which are being prepared and sold at pH less than 7 inspite of having N-acyl glycinates in it. US Pub. No. 2012/0046210 by Patel et. al. reports isotropic formulations having pH 7 and containing N-acyl glycinates, however these formulations are made possible by the incorporation of other ingredients such as polyols, glycosides, and polymers in the formulation. The other way of achieving isotropic formulations using N-acyl glycinate salts is to use very little amount of the same so that at skin pH the converted carboxylic acid form i.e. N-acyl glycine does not affect much to the isotropicity of the formulation. Pears® Oil Clear Glow Facewash (Unilever) and Lunamer® Clear Wash (Fuji Film Healthcare Laboratory, Japan) are some of the clear cleansers containing sodium cocoyl glycinate. However, in order to exploit all the advantageous properties and benefits of N-acyl glycinates, it has to be incorporated as a primary surfactant in high concentration in the cleansing compositions.

Therefore, it is a challenge to surfactant manufacturers and formulators to incorporate N-acyl glycinates as primary surfactants i.e. used in a quantity equal to or higher than other surfactants and still get a clear or transparent i.e. isotropic personal cleansing compositions having skin pH i.e. pH 5.0 to 6.0 and without using any additional non-surfactant ingredients such as polyols, glycosides, polymers, etc. This challenge has been overcome by the inventors of the present invention. The inventors have been able to solubilize N-acyl glycinates through novel aqueous cleansing compositions those remain isotropic at pH less than 7; more specifically at skin pH. Unlike reported in US Pub. No. 2012/0046210 by Patel et. al, the aqueous isotropic cleansing compositions of the present application do not contain any additional non-surfactant ingredient and are flowable at both low and high temperatures. These novel aqueous cleansing compositions are developed by combining N-acyl glycinates with O-acyl isethionates and specific solubilizing surfactants. This combination is surprising because it becomes extra challenging if a formulator or a surfactant manufacturer wants to combine N-acyl glycinates with the 'most difficult to soluble' surfactant i.e. O-acyl isethionates and still able to produce an aqueous cleansing composition which remains isotropic at skin pH.

O-acyl isethionates (salts) are yet other anionic surfactants having the general formula

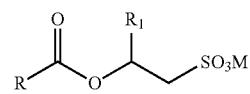

wherein, R is selected from C5 to C22 alkyl group, saturated or unsaturated, R1 is selected from H or methyl, and M is a cation selected from Li+, Na+, K+, NH4+ or a quaternary ammonium cation derived from tertiary amines.

O-acyl isethionates are highly desirable in skin and hair cleansing products, because they lather well, are mild to the skin and have good emollient and other sensory properties. Even relatively small amounts of O-acyl isethionates can contribute to these benefits. The cleansing and moisturization were combined first time in 1950s with the launch of DOVE® soap which was a game changing for the personal care industry with the advent of O-acyl isethionates. However, the significant limitation of O-acyl isethionates is their very poor solubility in water e.g. sodium cocoyl isethionate has only 0.01% solubility in water at 25° C. (page 2 of "Assessment Plan for Fatty acids, coco, sulfoethyl esters, sodium salts (sodium cocoyl isethionate)" prepared by Keller and Heckman LLP, November 2006).

To overcome this difficulty of incorporation of alkali metal O-acyl isethionates due to their poor solubility, researchers have created formulator-friendly compositions wherein alkali metal salts of O-acyl isethionates are solubilized in aqueous medium with the help of other surfactants and hence remain fluid and easy to incorporate (cold mixing) in the personal care formulations. U.S. Pat. No. 5,415,810 (Lever Brothers, Lee et al.) discloses the blends of O-acyl isethionates, zwitterionic surfactants and other anionic surfactants wherein the zwitterionic surfactant assists in the dissolution of O-acyl isethionate. U.S. Pat. No. 5,925,603 (Rhodia, Paul D'Angelo) reports blend of O-acyl isethionates, alkyl imidazoline amphoteric surfactants and anionic surfactants. US Pub. No. 2009/0062406 (Clariant, Matthias Loeffler) teaches aqueous concentrated blends wherein O-acyl isethionates are made deliverable with N-acyl taurate and betaines. U.S. Pat. No. 7,879,780 (Conopco Inc., Tsaur) reports combining O-acyl isethionates with betaines and sulphosuccinates. There are many such blends commercially available, viz. 1) ChemorylTMSFB, Lubrizol (sodium cocoyl isethionate, laureth sulphosuccinate and cocomidopropyl betaine), 2) Hostapon SCB, Clariant (sodium cocoyl isethionate, and cocobetaine) and 3) Miracare Plaisant, Solvay-Rhodia (sodium cocoyl isethionate, cocoamphoacetate, and sodium cocoyl taurate).

Tsaur et al. (Conopo, Inc.) in U.S. Pat. No. 8,263,538, U.S. Pat. No. 8,268,767, and U.S. Pat. No. 8,105,994, have reported the first time an exceptional synergistic combination of O-acyl isethionates and N-acyl glycinates to deliver 'super mildness' and 'skin benefits'. Although, these surfactant compositions have been claimed to be 'super-mild' to skin as proved by standard patch test on human volunteers, it is not reported that the compositions are isotropic in appearance at pH less than 7. The Dove's NutriumMoisture® ranges of products containing these super mild surfactant blends are opaque in appearance. Jawale et al. (Galaxy Surfactants Ltd) in US Pub. No. 2013/0189212 reported an isotropic blend of these two mild surfactants by combining them with alkyl betaines. However, this patent application teaches to use N-acyl glycinates in very low amount which is always far less than O-acyl isethionates. Further, if N-acyl glycinate is used in a quantity equal to or higher than O-acyl isethionate then it results into composition which is not isotropic i.e. hazy. In addition the clear blends of this patent application can only be made by using specific betaines i.e. alkyl betaines.

Thus, even after having significant difficulties in incorporating N-acyl glycinates and O-acyl isethionates in aqueous compositions as explained above, the inventors of the present invention have surprisingly created an aqueous cleansing composition which acts as a vehicle to solubilize N-acyl glycinate as a primary surfactant at skin pH, by combining it with O-acyl isethionate and a solubilizing surfactant in a unique method.

These and other aspects, features and advantages will become apparent in the following description, drawings and the appended claims.

As explained in the background of the invention, there was a need to solubilize N-acyl glycinates in aqueous form which should remain isotropic i.e. transparent at pH less than 7, more preferably at skin pH i.e. pH 5.0 to 6.0, and this is achieved through novel aqueous cleansing compositions of the present invention. These aqueous cleansing compositions help to solubilize N-acyl glycinate as a primary surfactant and remain isotropic and flowable even at skin pH. These aqueous cleansing compositions are prepared by combining N-acyl glycinates with O-acyl isethionates and at least one solubilizing surfactant, in a unique method.

As mentioned in the prior art, the compositions comprising O-acyl isethionates, N-acyl glycinates, and amphoteric/zwitterionic surfactants were well established by Tsaur et al. (U.S. Pat. No. 8,263,538, U.S. Pat. No. 8,268,767, and U.S. Pat. No. 8,105,994) and Jawale et al. (US Pub. No. 2013/0189212). Tsaur et al. do not report anything about the isotropicity of the said compositions. However, it is proved by the inventors of the present invention that such compositions are not isotropic at pH less than 7. The comparative Examples 6A to 12A (given in the Examples of present invention) represents similar composition comprising sodium cocoyl glycinate, sodium cocoyl isethionate, and cocoamidopropyl betaine/sulfobetaine as claimed in U.S. Pat. No. 8,263,538 and U.S. Pat. No. 8,268,767, and it was found that these compositions remain opaque at and below pH 6.0.

US Pub. No. 2013/0189212 by Jawale et al. reports an isotropic blend of O-acyl isethionates, N-acyl glycinates, and alkyl betaines. However, the inventors of the present invention have identified following aspects in this prior art.

It relates to solubilization of O-acyl isethionates. It teaches to use N-acyl glycinates in a very low amount and is always far less than O-acyl isethionates and alkyl betaines (Examples 1 to 9, page no. 5 of US Pub. No. 2013/0189212).

If N-acyl glycinate is used as primary surfactant i.e. N-acyl glycinate used in quantity equal to or higher than O-acyl isethionates and/or all other surfactants present in the composition then it results into compositions which are hazy or opaque. This was proved by the inventors of the present invention in the Examples 27A to 30A.

The isotropic (clear) blends of this prior art can only be made by using specific betaines i.e. alkyl betaines. Alkyl betaines such as Lauryl betaine and Coco betaine are produced by reacting fatty dimethyl amines with chloroacetic acid. The fatty dimethyl amines are very expensive tertiary amines and hence it makes the final product 'alkyl betaines' expensive which costs around 2.5 USD/kg which is much higher than the commonly used betaine i.e. cocamidopropyl betaine which costs around 1.0 USD/kg only. Thus, surfactants like alkyl betaines definitely make the final formulations less competitive in terms of cost.

Tsaur et al., and Jawale et al. teach preparation of surfactant blends by mixing O-acyl isethionates, N-acyl glycinates, and amphoteric surfactants in their individual physical forms. Present inventors have found that blending of N-acyl glycinates and O-acyl isethionates in their individual physical forms is one of the significant reasons for failing to achieve an isotropic aqueous cleansing composition if N-acyl glycinate need to be present as a primary surfactant. This limitation of using individual physical form of surfactants was suitably removed by a process wherein the aqueous blend of N-acyl glycinates and O-acyl isethionates is synthesized from same fatty acid chloride by reacting with alkali metal isethionate first and then with alkali metal glycine in a sequential manner. This process is described in the copending application PCT/IN2013/000494 (Koshti et al.). However, although this process avoids the use of individual physical forms of N-acyl glycinates and O-acyl isethionates, it does not provide aqueous composition comprising N-acyl glycinate as a primary surfactant and still remain isotropic at skin pH. The blends prepared by this process of Koshti et al turn hazy or opaque if the pH is reduced to less than 7 at ambient temperature i.e. 25° C. (refer Comparative Examples 25A and 26A)

After further researching on the subject, the inventors of the present invention have unexpectedly found that by the addition of at least one solubilizing surfactant to the aqueous blends of N-acyl glycinates and O-acyl isethionates prepared as per the process of Koshti et al., it result in aqueous cleansing compositions which remain isotropic i.e. clear and transparent at pH less than 7.0, more preferably at skin pH and at ambient temperature. Thus, the present invention provides solubilization of N-acyl glycinates through a novel aqueous cleansing composition comprising N-acyl glycinates, O-acyl isethionates, and solubilizing surfactants wherein the aqueous cleansing composition remains isotropic and flowable at skin pH and at temperature 25° C. An important aspect of the present invention is that N-acyl glycinate is present in the composition as a primary surfactant i.e. the quantity of N-acyl glycinate in the composition is always equal to or more than O-acyl isethionate. It was never possible through the teachings of prior art to prepare such an aqueous skin pH cleansing composition having such high amount of N-acyl glycinate and remain isotropic and flowable at ambient temperature i.e. 25° C. It is further achieved through the present invention that N-acyl glycinate is contained as a primary surfactant along with an insoluble surfactant i.e. O-acyl isethionate and the aqueous composition still stays isotropic at skin pH.

Accordingly, the present invention relates to aqueous cleansing compositions comprising:

aqueous blend of N-acyl glycinates of Formula I, and O-acyl isethionates of Formula II;

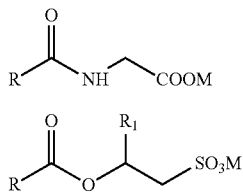

Formula I

Formula II wherein,

R is selected from $C_5$ to $C_{22}$ alkyl group, saturated or unsaturated, $R_1$ is selected from H or methyl, and M is a cation selected from $Li^+$, $Na^+$, $K^+$, $NH4^+$ or a quaternary ammonium cation derived from tertiary amines;

prepared by the process comprising steps of

A) reacting more than one equivalent of fatty acid chloride with alkali metal or ammonium salts of hydroxyalkyl sulphonates to prepare compounds of Formula II, B) reacting the product of step (A) (containing the remainder fatty acid chloride) with glycine in the presence of a base under typical aqueous Schotten Baumann reaction conditions to form compounds of Formula I.

wherein the weight ratio of N-acyl glycinates of Formula I to O-acyl isethionates of Formula II is in range of 1.0:1.0 to 10.0:1.0, and (ii) a solubilizing surfactant wherein the weight ratio of (i):(ii) is from 1.0:0.1 to 1.0:1.0, and wherein said aqueous cleansing compositions are isotropic and flowable at skin pH.

Thus, the present invention provides a surfactant composition wherein N-acyl glycinate is present as primary surfactant in comparison with any other surfactant present in the composition. It is also made possible by the present invention to obtain composition wherein N-acyl glycinate is present as primary surfactant in comparison with all other surfactants put together. Accordingly to an embodiment of the present invention, the ratio of N-acyl glycinates to O-acyl isethionates and solubilizing surfactant is from 1.0:0.1 to 1.0:1.0. For example if N-acyl glycinate is 15% by wt. then both O-acyl isethionate and solubilizing surfactant together shall be 15% maximum.

The solubilizing surfactant(s) suitable for the present invention is selected from amphoteric surfactants, nonionic surfactants, and anionic surfactants other than O-acyl isethionates and N-acyl glycinates, and mixtures thereof. These surfactants are explained in details as follows.

Amphoteric Surfactants

Amphoteric surfactants which can be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

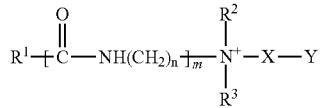

where $R_1$ is alkyl or alkenyl of 7 to 18 carbon atoms;

$R^2$ and $R^3$ are each independently alkyl, hydroxyalkyl or carboxyalkyl of 1 to 3 carbon atoms;

n is 2 to 4;

m is 0 to 1;

X is alkylene of 1 to 3 carbon atoms optionally substituted with hydroxyl, and Y is —$CO_2$— or —$SO_3$—

Alkylamphoacetates and dialkylamphoacetates are also intended to be covered among possible amphoteric compounds which can be also used.

Examples of suitable amphoteric surfactants are alkyl betaines; amidoalkyl betaines; amphocarboxylate derivatives such as (mono or di) alkylamphoacetate; and amidoalkyl sultaines.

Cocamidopropyl betaine commercially available as Galaxy CAPB, lauramidopropyl betaine commercially available as Galaxy LAPB, cocamidopropyl hydroxysultaine commercially available as Galaxy CAPSB, lauryl betaine, lauroamphoacetate, cocoamphoacetate, cocoamphopropionate, and lauryl hydroxysultaine, are particularly useful and preferred amphoteric surfactants for the present invention. If required coco-betaine commercially available as Galaxy CB can also be used in combination.

Nonionic Surfactants

This class of surfactants includes alkyl and alkenyl polysaccharides. Preferred alkyl or alkenyl polysaccharides are of the formula:

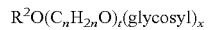

wherein R2 is selected from the group consisting of alkyl, alkenyl, alkylphenyl, hydroxyalkyl, hydroxyalkylphenyl, and mixtures thereof in which alkyl or alkenyl groups contain from about 8 to about 18, preferably from about 12 to about 14, carbon atoms; n is 0 to 3, preferably 2; t is form 0 to about 10, preferably 0; and x is from 1 to about 10, preferably from 1.1 to about 3.0. The glycosyl is preferably derived from glucose. Preferred alkyl polyglycosides that can be used are lauryl glucoside, capryl glucoside, coco glucosides, and decyl glucoside, and also mixed alkyl polyglycosides such as caprylyl/capryl glucoside, lauryl/myristyl glucoside, and caprylyl/myristyl glucoside. The commercially available alkyl and alkenyl polysaccharides are GLUCOPON® series, PLANTACARE® series, PLANTAREN® series, and AGNIQUE® PG series all by BASF, TRITON® series by Dow, ELOTANT Milcoside series by LG Household & Health Care. The preferred polysaccharides that can be used in the present invention are ELOTANT Milcoside 100, ELOTANT Milcoside 200, and ELOTANT Milcoside 300 series.

Other nonionic surfactants which may be used include in particular the reaction products of compounds having a hydrophobic group and a reactive hydrogen atom, for example aliphatic alcohols, acids, amides or alkyl phenols with alkylene oxides, especially ethylene oxide either alone or with propylene oxide. Specific nonionic detergent compounds are the condensation products of aliphatic ($C_8$-$C_{18}$) primary or secondary linear or branched alcohols with ethylene oxide, the alkyl ($C_6$-$C_{22}$) phenols-ethylene oxide condensates, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides. The nonionic may also be a sugar amide, such as a polysaccharide amide.

Anionic Surfactants

Anionic surfactants which can be used in this invention include alkyl sulfate or alkyl ether sulfate (including alkyl glyceryl ether sulfates). Among the alkyl sulfates are those having the formula: ROSO3M and alkyl ether sulfates are those having the formula: $RO(CH_2CH_2O)_n SO_3M$ wherein R is an alkyl or alkenyl having 8 to 18 carbons, preferably 12 to 18 carbons, and more preferably 12 to 14 carbons, n has an average value of greater than at least 0.5, preferably between 1 and 3; and M is a cation such as sodium, potassium, ammonium or substituted ammonium. The preferred anionic surfactants are alkyl ether sulfates such as sodium lauryl ether sulfates having average 1 mole ethoxylation and is commercially available as Galaxy LES 170 (70% active) sodium lauryl ether sulfates having average 2 mole ethoxylation and is commercially available as Galaxy LES (70% active) and Galaxy LES (28% active), sodium lauryl ether sulfates having average 3 mole ethoxylation and is commercially available as Galaxy LES 370 (70% active) and Galaxy LES 328 (28% active).

Other anionic surfactants which can be used include aliphatic sulfonates, such as a primary alkane (e.g., $C_8$-$C_{22}$) sulfonates, primary alkane (e.g., $C_8$-$C_{22}$) disulfonate, $C_8$-$C_{22}$ alkene sulfonate, $C_8$-$C_{22}$ hydroxyalkane sulfonate or alkyl glyceryl ether sulfonate (AGS); or an aromatic sulfonate such as alkyl benzene sulfonate.

Alkyl sulfosuccinates and ethoxylated alkyl sulfosuccinates (including mono- and dialkyl, e.g., $C_6$-$C_{22}$ sulfosuccinates) those can be used in the present invention are as disodium lauryl sulfosuccinate commercially available as Galaxy LSS, disodium laureth sulfosuccinate commercially available as Galaxy ESS, alkyl sulfoacetates, C8-C22 monoalkyl succinates and maleates.

Other Ingredients:

In addition to the amphoteric and/or anionic surfactants the aqueous cleansing composition of the present invention can depending on the embodiment comprise one or more of cationic surfactants. Many cationic surfactants are known in the art and almost any cationic surfactant is suitable for optional use in the present invention. The aqueous cleansing composition may contain various preservatives, conditioning agents, fragrances, benefit agents, etc., as known in the art.

According to an embodiment, the present invention also relates to a process for preparing the isotropic aqueous cleansing composition to solubilize N-acyl glycinates at skin pH. The process involves:

preparing aqueous blend of N-acyl glycinates of Formula I, and O-acyl isethionates of Formula II, by

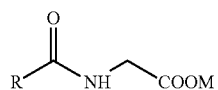

Formula I

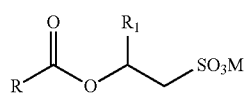

Formula II

A) reacting more than one equivalence of fatty acid chloride with alkali metal or ammonium salts of hydroxyalkyl sulphonates to prepare compounds of Formula II, B) reacting the product of step (A) (containing the remainder fatty acid chloride) with glycine in the presence of a base (e.g. hydroxides or carbonates of lithium, potassium, sodium and ammonium) under typical aqueous Schotten Baumann reaction conditions to form compounds of Formula I;

(i) adding at least one solubilizing surfactant to the aqueous blend at room temperature; and (ii) adjusting the pH of the mixture to less than 7.0, preferably between pH 5 to 6.

It is also an advantage of the present invention that it does not require any heating of the surfactants as compared to the processes reported in the patents of Tsuar et al. and in the patent application of Jawale et al. This heating is due to the use of SOLID forms of salts of O-acyl isethionates that are available in the form of needles, pastille, flakes, powder or granules. Moreover, making solid form of O-acyl isethionates itself involves a reaction at 225° C. and handling of molten mass to convert that into solid of desired physical form involves complex technology to ensure there is no deterioration of bulk of the molten mass at very high temperature. Also, with every solid form (granule, powder or prill) of O-acyl isethionate that is produced there is a certain degree of dusting associated and that warrants special precaution as inhalation of this dust is a serious health hazard. The manufacturers of liquid surfactant compositions have to deal with dissolution of hard, virtually water-insoluble, high-melting (above 200° C.) O-acyl isethionates. This is done by heating and mixing solid O-acyl isethionates with other surfactants, either anionic or amphoteric or both as explained in the background of this invention.

Further, the patents by Tsuar et al. require use of only critically defined fatty acid isethionate products i.e. greater than 25% and less than 45% of the fatty acyl isethionate should be of chain length C16 or greater; and greater than 50% of chain length of free fatty acid and fatty acid soap groups combined should be of chain length C16 to C20 (as is described in U.S. Pat. No. 8,124,574) to form unique ultra mild surfactant compositions by synergistically reacting with alkanoyl surfactants (N-acyl amino acid based surfactants). Further, U.S. Pat. No. 5,415,810 (Lever Brothers, Lee et al.) reports that O-acyl isethionate and other surfactants containing C16 and higher carbon atoms should be absent as these surfactants do not readily enter into aqueous solution and therefore do not provide clear compositions. A solution provided by U.S. Pat. Nos. 7,655,607 & 7,674,759 (both filed by Conopco, Tsuar et al.) teaches to use specific combinations of high levels of liquid crystal inducer or temperature stabilizers (e.g., alkanolamide) and liquid crystal modifier (e.g. predominantly straight chain fatty acid) or in order to provide acyl isethionate compositions that are stable at both low and elevated temperature storage, regardless of the fatty acid content or fatty acid chain length of the acyl isethionates surfactant. Thus, prior art requires that fatty acid profile of O-acyl isethionates is also a critical factor and it affects the isotropy or clarity and benefits of the O-acyl isethionate compositions. This limitation of fatty acid profile has been overcome by the present invention which allows preparing aqueous cleansing compositions those are stable at both low and elevated temperatures regardless of the fatty acid content or fatty acid chain length of the O-acyl isethionates and without any worry of having any additional inducing agents or modifiers/stabilizers.

As per present invention, the weight ratio of (i) aqueous blend of N-acyl glycinates and O-acyl isethionates, to (ii) solubilizing surfactant is from 1.0:0.1 to 1.0:1.0. Solubilizing surfactant is an additional surfactant and the present invention facilitates to maintain these solubilizing surfactants less than the active surfactants i.e. N-acyl glycinate and O-acyl isethionate.

Yet another advantage of the present invention is that the total solids content or active content of the mild surfactants (N-acyl glycinates, O-acyl isethionates, and solubilizing surfactants) in the novel aqueous cleansing composition can be adjusted to any desired level. However, the preferred range of solids content with good isotropy and flowability is between 1 to 50% by wt.; the most preferred range is between 10-45% by wt. As explained herein before, the pH of the novel aqueous cleansing composition is very important for the present invention since it relates to solubilization of N-acyl glycinates at skin pH i.e. between pH 5.0 to 6.0.

The aqueous cleansing compositions of the present invention can be stored at extended time periods at room, elevated and cold temperatures without precipitation or decomposition of N-acyl glycinates and O-acyl isethionates. These novel compositions do not contain any solvent except water; also they do not contain any additional non-surfactant ingredients. This feature of the cleansing composition is unique because it will help the formulators to create their required personal care/cleansing formulation using their own desired additional ingredients.

The novel aqueous cleansing compositions of the present invention can be regarded as multifunctional surfactant blend which is isotropic i.e. transparent, mild, foaming and capable of moisturization as well. These performance characteristics of the present novel aqueous cleansing composition are explained as follows.

Moisturization:

The aqueous cleansing compositions advantageously provide enhanced and synergistic moisturization as compared to blend of Jawale et al wherein the surfactants are externally mixed i.e. they are mixed in their individual physical forms. Example B shows a moisture retention capacity of inventive aqueous cleansing compositions on hair.

Foaming:

Despite the excellent moisturization properties of the composition, it also demonstrates good creamy foaming. In general, the amount of foam generated by a cleansing composition is directly related to its perceived cleansing efficacy. The greater is the volume of foam produced and the greater is the stability of the foam; the more efficient is the perceived cleansing action. Surprisingly, it has been found that the aqueous cleansing compositions of the present invention exhibits better foam behaviour than individual component surfactants of the same concentration. The presence of a synergistic foaming effect in aqueous cleansing composition was demonstrated by foam measurements (Hart De George method) as exemplified in Example C.

Sensory Benefits:

The inventive aqueous cleansing composition also provides a very good sensory feel to the skin and is illustrated in Example D.

According to an embodiment, the novel aqueous cleansing compositions of the present invention can be used directly as a final personal care/cleansing formulation or can be incorporated into personal care/cleansing formulations along with other desired ingredients to prepare shampoos, hand soaps, body washes, face washes, hand washes, shower gels, baby bubble bath, and the like. Hence, formulators of personal care products will find many advantages in using this inventive aqueous cleansing composition. The present invention also facilitates to prepare all types of personal care formulations depending upon the need; it is possible to prepare sulfate-free, mild personal cleansing compositions using the inventive aqueous cleansing compositions as exemplified in Example E.

One of the key merits of the aqueous cleansing composition of the present invention is its optimum viscosity; is easy to handle and can be processed even in cold conditions. Further, personal care formulations such as shampoos required to have a particular viscosity so that the liquid solution does not flow easily so as to reach to the eyes but stays on the hair. The viscosity of the aqueous cleansing compositions of the present invention preferably ranges between 500-10,000 cps. Thus, it is viscous enough to give the final formulation, the desired viscosity without using any polymeric viscosity enhancers and also it is not very much viscous to behave like a non-flowable gel type material.

Some Advantages (Benefits) of the Present Invention

The inventive aqueous cleansing composition acts as a primary source of N-acyl glycinates for preparing isotropic skin pH personal cleansing formulations.

The inventive aqueous cleansing compositions remain isotropic i.e. transparent and flowable at pH 5.0-6.0 which is the pH of human skin also called skin pH.

N-acyl glycinate is present as a primary surfactant in the novel aqueous cleansing composition, wherein the weight ratio of N-acyl glycinate to O-acyl isethionate is 1:1 or higher i.e. N-acyl glycinate is present in an amount equal to or higher than O-acyl isethionate.

It facilitates to use solubilizing surfactant(s) in a quantity equal to or less than N-acyl glycinate and O-acyl isethionate which is not possible in prior art (e.g. Jawale et al teaches to use cocobetaine always more than Sodium Cocoyl Glycinate and Sodium Cocoyl isethionate).

Provides flexibility in using various types of solubilizing surfactants i.e. nonionic, anionic, amphoteric surfactants, and is not restricted to a specific surfactant (e.g. Jawale et al. teaches to use only alkylbetaines).

It provides use of cheapest solubilizing surfactants such as Cocamidopropyl Betaine, Sulfosucinnates, etc. which is not possible in the prior art (e.g. Jawale et al teaches to use only alkylbetaines which are very expensive).

N-acyl glycinate is made solubilized at skin pH in the novel aqueous cleansing compositions which also contain another highly insoluble surfactant i.e. O-acyl isethionates. O-acyl isethionate is another useful mild surfactant desired by formulators.

The novel aqueous cleansing compositions remain isotropic and flowable at skin pH even if the concentration of total surfactant is very high i.e. upto 45-50% by wt.

Provides synergistic sensory, moisturization, and foaming properties to the formulation.

The isotropic aqueous cleansing composition of the present invention can also be spray dried and a homogenous powder is obtained. On dissolution of this spray dried powder of these two types of surfactants in water with the original solids level results in clear solution with the same chemical composition. Thus, the blend of cleansing composition in the dry form can be easily obtained by routine spray-drying operation. Cleansing composition in the solid form can be desired in certain applications where water is to be avoided e.g. solid soap bar.

All the quantities given in percentage (%) are, unless otherwise stated, on the "active" basis rather than on the "as is" basis as purchased from the supplier. The "active" basis, thus, does not include any impurity, side product or diluent that may be present in that ingredient.

EXAMPLES

It should be understood that although these examples may describe, in more particular detail, some of the very specific features of the invention, they are given primarily for purposes of illustration and the invention in its broader aspects is not to be construed as limited thereto.

The novel aqueous cleansing compositions of the present invention are prepared in following two steps:

Step 1. Synthesis of aqueous blend of N-acyl glycinates and O-acyl isethionates.

It comprises of:

reacting more than one equivalence of fatty acid chloride with alkali metal or ammonium salts of hydroxyalkyl sulphonates to prepare compounds of Formula II, and reacting the product of step (A) (containing the remainder fatty acid chloride) with glycine in the presence of a base (e.g. hydroxides or carbonates of Lithium, potassium, sodium and ammonium) under typical aqueous Schotten Baumann reaction conditions to form compounds of Formula I.

Various aqueous blends having varying ratio of N-acyl glycinates and O-acyl isethionates can be prepared as taught by Koshti et al. (Galaxy Surfactants Ltd.) in his copending application PCT/IN2013/000494 patent application WO2014181342. This is explained in Example 1 of the present invention.

Step 2. Mixing the aqueous blend of step 1 with a solubilizing surfactant.

It comprises of:

Adding the solubilizing surfactant to the aqueous blend of step 1 to form a mixture.

Adjusting pH of the mixture to 5.0 to 6.0 (skin pH) with suitable acid.

This is explained in Example 2 of the present invention.

For the ease of describing the examples, following acronyms/trade names are used within the scope of the present invention GI: Aqueous blend of sodium N-cocoyl glycinate and sodium O-cocoyl isethionate as made according to procedure described in Example 1.

SCG: Sodium N-cocoyl Glycinate. Galsoft SCG (24% active) sold by Galaxy Surfactants Ltd. is used.

SCI: Sodium O-cocoyl Isethionate. Galsoft SCI 80 (80% active) sold by Galaxy Surfactants Ltd. is used.

LAPB: Lauramidopropyl betaine. Galaxy LAPB (30% active) sold by Galaxy Surfactants Ltd. is used.

CAPSB: Cocamidopropyl sulfobetaine. Galaxy CAPSB (40% active) sold by Galaxy Surfactants Ltd. is used.

CAPB: Cocamidopropyl betaine. Galaxy CAPB (36% active) sold by Galaxy Surfactants Ltd. is used.

SLES: Sodium Lauryl Ether Sulfate. Galaxy LES (28% active, 2 mole EO) is used.

ESS: Disodium Laureth Sulfosuccinate. Galaxy ESS (~38% active) is used.

ELOTANT Milcoside 100: C8-10 alkyl polyglucoside.

ELOTANT Milcoside 301: C8-14 alkyl polyglucoside.

ELOTANT Milcoside 302: C8-14 alkyl polyglucoside/Decyl-Glucoside.

ELOTANT Milcoside 303: C8-14 alkyl polyglucoside.

Example 1

Synthesis of Aqueous Blend of Sodium N-Cocoyl Glycinate and Sodium O-Cocoyl Isethionate (GI)

This is prepared as taught by Koshti et al. (Galaxy Surfactants Ltd.) in his patent application WO2014181342.

The cocoyl chloride used in this experiment has the following alkyl chain distribution $C_8$: 5.0%
$C_{10}$: 6.0%
$C_{12}$: 63%
$C_{14}$: 20%
$C_{16}$: 6%
$C_{18}$: 0.4%

Fatty acid chlorides are preferably prepared as per the procedure reported in the Patent Application (WO/2014/030038) by Koshti et al. (Method to produce N-acyl amino acid surfactants using N-acyl amino acid surfactants or corresponding anhydrides as catalyst).

To a stirred cocoyl chloride (234 g, 1.05 gmol) under slow purging of nitrogen at room temperature, sodium isethionate (52 g, 0.35 gmol) was added and the slurry was stirred at 55-60° C. for 4 h. The HCl gas generated was absorbed in alkali solution and the progress of reaction was monitored by IR spectrum analysis. The FTIR spectrum of the intermediate showed the presence of unreacted cocoyl chloride (carbonyl stretch at 1800 $cm^{-1}$), sodium cocoyl isethionate (carbonyl of ester at 1734 $cm^{-1}$) and disappearance of hydroxyl stretch (3323 $cm^{-1}$) of sodium isethionate.

This fluid viscous reaction mass (270 g) was cooled to room temperature and then added slowly to a stirred aqueous solution of glycine (53.55 g, 0.71 gmol) in water (730 g) along with sodium hydroxide solution (48.8%, 116 g, 1.41 gmol) simultaneously while maintaining the pH of the reaction mass between 10.2 to 10.5 and the temperature between 20 to 30° C. The addition was completed in two hours and the reaction mass was stirred for another 4 h at 25° C. The pH was adjusted to 7.5 with HCl. The solids content of the reaction mass was adjusted to 30% solids content to yield 1169 g of aqueous solution product.

IR spectrum of dried sample showed carbonyl stretch of amide at 1600-1620 $cm^{-1}$ and NH stretch at 3344 $cm^{-1}$. The other significant stretching frequencies were carbonyl of ester of alkanoyl isethionate at 1734 $cm^{-1}$ and total disappearance of carbonyl stretching frequency (1800 $cm^{-1}$) of cocoyl chloride. The analysis of the above aqueous surfactant blend was as follows

| Test | Results |
| --- | --- |
| Appearance | Light yellow clear liquid |
| Viscosity at 25° C. | 400 cps |
| pH as such | 7.5 |
| NaCl, % w/w | 3.70 |
| Total solids, % w/w | 31.00 |
| Sodium N-cocoyl Glycinate, % w/w | 14.00 |
| Sodium O-cocoyl Isethionate, % w/w | 8.40 |
| Wt. ratio of sodium N-cocoyl glycinate:sodium O-cocoyl isethionate | 1.67:1 |

The above example describes the preparation of GI with the weight ratio 1.67:1. Similarly various aqueous blends having varying weight ratio of N-acyl glycinates and O-acyl isethionates such 2:1, 1:1, 3:1, 5:1, 10:1 and like can be prepared using this procedure.

Example 2

Mixing the aqueous blend of Example 1 with a solubilizing surfactant. This is done by conducting the following steps:

Adding solubilizing surfactant to the aqueous blend of step 1 (example 1) to form a mixture; and Adding water, if required, to adjust the solids content and/or to make the total quantity to 100%; and Adjusting the pH of the mixture to 5.0 to 6.0 (skin pH) with 50% citric acid solution.

The novel aqueous cleansing compositions, with different surfactant concentrations and different skin pH, of the present invention are prepared using the same procedures of Example 1 and 2 with only change in quantities of reactants as per requirement. The results (analysis) of these inventive compositions are set forth in Examples 3 to 20. It is clearly seen that all the inventive compositions contain N-acyl glycinates as primary surfactants and remain clear, flowable at skin pH (5.0-6.0). Example 3, 4 and 5 are the results of inventive compositions having high active content (or high solid content) and they still remain clear, low viscous, flowable at skin pH. Results of comparative compositions are given in Examples 3A to 30A.

Example 3 to 5

These compositions are prepared using ELOTANT Milcoside 100 and ESS as a solubilizing surfactant.

| Aqueous cleansing composition | Ex. 3* | Ex. 4 | Ex. 5 |
|---|---|---|---|
| 1. GI | 20.00% | 15.00% | 15.00% |
| a. SCG in GI | 13.33% | 7.50% | 7.50% |
| b. SCI in GI | 6.66% | 7.50% | 7.50% |
| 2. ELOTANT Milcoside 100 | 20.00% | 15.00% | — |
| 3. ESS | — | — | 15.00% |
| Wt. ratio of SCG:SCI (in GI) | 2:1 | 1:1 | 1:1 |
| Wt. ratio of GI:ELOTANT Milcoside 100 | 1:1 | 1:1 | — |
| Wt. ratio of GI:ESS | — | — | 1:1 |
| Total solids | 44.09% | 31.06% | 29.53% |
| NaCl | 3.05% | 1.9% | 1.95% |
| pH (as such) | 6.0 | 5.5 | 6.0 |
| Viscosity at 25° C. | 3500 cps | 720 cps | 3560 cps |
| NTU** | 9.5 | 5.2 | 4.17 |
| Appearance @ 25° C. | Isotropic | Isotropic | Isotropic |

*GI is used in its solid (powdered) form in this example.
**The measurements are shown in Nephelometric Turbidity Units (NTU). The readings were all taken in the 000-999 NTU range which was calibrated daily. Readings of less than 400 NTU are considered clear; greater than 400 NTU are considered translucent; and readings under 100 NTU are considered water clear and optically isotropic.

Example 6 to 10

These compositions are prepared using CAPSB as a solubilizing surfactant.

| Aqueous cleansing composition | Ex. 6 | Ex. 7 | Ex. 8 | Ex. 9 | Ex. 10 |
|---|---|---|---|---|---|
| 1. GI | 2.5% | 7.0% | 6.0% | 3.0% | 3.5% |
| a. SCG in GI | 1.25% | 3.5% | 3.0% | 1.5% | 1.75% |
| b. SCI in GI | 1.25% | 3.5% | 3.0% | 1.5% | 1.75% |
| 2. CAPSB | 2.5% | 7.0% | 6.0% | 3.0% | 3.5% |
| Wt. ratio of SCG:SCI (in GI) | 1:1 | 1:1 | 1:1 | 1:1 | 1:1 |
| Wt. ratio of GI:CAPSB | 1:1 | 1:1 | 1:1 | 1:1 | 1:1 |
| pH (as such) | 5.5 | 6.0 | 6.0 | 5.5 | 5.5 |
| Appearance @ 25° C. | Isotropic | Isotropic | Isotropic | Isotropic | Isotropic |

Comparative Example 6A to 10A

These compositions are prepared by using CAPSB as a solubilizing surfactant and wherein all the surfactants are mixed in their individual physical forms

| Aqueous cleansing composition | Ex. 6A | Ex. 7A | Ex. 8A | Ex. 9A | Ex. 10A |
|---|---|---|---|---|---|
| 1. SCG | 1.25% | 3.5% | 3.0% | 1.5% | 1.75% |
| 2. SCI | 1.25% | 3.5% | 3.0% | 1.5% | 1.75% |
| 3. CAPSB | 2.5% | 7.0% | 6.0% | 3.0% | 3.5% |
| Wt. ratio of SCG:SCI | 1:1 | 1:1 | 1:1 | 1:1 | 1:1 |
| Wt. ratio of (SCG + SCI):CAPSB | 1:1 | 1:1 | 1:1 | 1:1 | 1:1 |
| pH (as such) | 5.5 | 6.0 | 6.0 | 5.5 | 5.5 |
| Appearance @ 25° C. | Opaque | Opaque | Opaque | Opaque | Opaque |

Example 11 to 14

These compositions are prepared using CAPB and SLES as a solubilizing surfactant

| Aqueous cleansing composition | Ex. 11 | Ex. 12 | Ex. 13 | Ex. 14 |
|---|---|---|---|---|
| 1. GI | 7.0% | 7.5% | 7.0% | 7.5% |
| a. SCG in GI | 3.5% | 5.0% | 3.5% | 5.0% |
| b. SCI in GI | 3.5% | 2.5% | 3.5% | 2.5% |
| 2. CAPB | 7.0% | 7.5% | — | — |
| 3. SLES | — | — | 7.0% | 7.5% |
| Wt. ratio of SCG:SCI (in GI) | 1:1 | 2:1 | 1:1 | 2:1 |
| Wt. ratio of GI:CAPB | 1:1 | 1:1 | — | — |
| Wt. ratio of GI:SLES | — | — | 1:1 | 1:1 |
| pH (as such) | 6.0 | 6.0 | 6.0 | 6.0 |
| Appearance @ 25° C. | Isotropic | Isotropic | Isotropic | Isotropic |

Comparative Example 11A to 14A

These compositions are prepared by using CAPB and SLES as a solubilizing surfactant and wherein all the surfactants are mixed in their individual physical forms

| Aqueous cleansing composition | Ex. 11A | Ex. 12A | Ex. 13A | Ex. 14A |
|---|---|---|---|---|
| 1. SCG | 3.5% | 5.0% | 3.5% | 5.0% |
| 2. SCI | 3.5% | 2.5% | 3.5% | 2.5% |
| 3. CAPB | 7.0% | 7.5% | — | — |
| 4. SLES | — | — | 7.0% | 7.5% |
| Wt. ratio of SCG:SCI | 1:1 | 2:1 | 1:1 | 2:1 |
| Wt. ratio of (SCG + SCI):CAPB | 1:1 | 1:1 | — | — |
| Wt. ratio of (SCG + SCI):SLES | — | — | 1:1 | 1:1 |
| pH (as such) | 6.0 | 6.0 | 6.0 | 6.0 |
| Appearance @ 25° C. | Opaque | Opaque | Opaque | Opaque |

Example 15 to 18

These compositions are prepared using Alkyl Polyglucoside as a solubilizing surfactant.

| Aqueous cleansing composition | Ex. 15 | Ex. 16 | Ex. 17 | Ex. 18 |
|---|---|---|---|---|
| 1. GI | 2.5% | 2.5% | 2.5% | 2.5% |
| a. SCG in GI | 1.25% | 1.25% | 1.25% | 1.25% |
| b. SCI in GI | 1.25% | 1.25% | 1.25% | 1.25% |
| 2. ELOTANT Milcoside 100 | 2.5% | — | — | — |
| 3. ELOTANT Milcoside 301 | — | 2.5% | — | — |
| 4. ELOTANT Milcoside 302 | — | — | 2.5% | — |
| 5. ELOTANT Milcoside 303 | — | — | — | 2.5% |
| Wt. ratio of SCG:SCI (in GI) | 1:1 | 1:1 | 1:1 | 1:1 |

-continued

| Aqueous cleansing composition | Ex. 15 | Ex. 16 | Ex. 17 | Ex. 18 |
|---|---|---|---|---|
| Wt. ratio of GI:Milcoside | 1:1 | 1:1 | 1:1 | 1:1 |
| pH (as such) | 5.2 | 5.52 | 5.3 | 5.3 |
| Appearance @ 25° C. | Isotropic | Isotropic | Isotropic | Isotropic |

Comparative Example 15A to 18A

These compositions are prepared using Alkyl Polyglucoside as a solubilizing surfactant and wherein all the surfactants are mixed in their individual physical forms.

| Aqueous cleansing composition | Ex. 15A | Ex. 16A | Ex. 17A | Ex. 18A |
|---|---|---|---|---|
| 1. SCG | 1.25% | 1.25% | 1.25% | 1.25% |
| 2. SCI | 1.25% | 1.25% | 1.25% | 1.25% |
| 3. ELOTANT Milcoside 100 | 2.5% | — | — | — |
| 4. ELOTANT Milcoside 301 | — | 2.5% | — | — |
| 5. ELOTANT Milcoside 302 | — | — | 2.5% | — |
| 6. ELOTANT Milcoside 303 | — | — | — | 2.5% |
| Wt. ratio of SCG:SCI | 1:1 | 1:1 | 1:1 | 1:1 |
| Wt. ratio of (SCG + SCI):Milcoside | 1:1 | 1:1 | 1:1 | 1:1 |
| pH (as such) | 5.2 | 5.52 | 5.3 | 5.3 |
| Appearance @ 25° C. | Opaque | Opaque | Opaque | Opaque |

Example 19 and 20

These compositions are prepared using Sulfosuccinate and LAPB as a solubilizing surfactants.

| Aqueous cleansing composition | Ex. 19 | Ex. 20 |
|---|---|---|
| 1. GI | 3.0% | 2.5% |
| a. SCG in GI | 1.5% | 1.25% |
| b. SCI in GI | 1.5% | 1.25% |
| 2. ESS | 3.0% | — |
| 3. LAPB | — | 2.5% |
| Wt. ratio of SCG:SCI (in GI) | 1:1 | 1:1 |
| Wt. ratio of GI:ESS (or LAPB) | 1:1 | 1:1 |
| pH (as such) | 5.5 | 5.5 |
| Appearance @ 25° C. | Isotropic | Isotropic |

Comparative Example 19A and 20A

These compositions are prepared using sulfosuccinate and LAPB as a solubilizing surfactant and wherein all the surfactants are mixed in their individual physical forms.

| Aqueous cleansing composition | Ex. 19A | Ex. 20A |
|---|---|---|
| 1. SCG | 1.5% | 1.25% |
| 2. SCI | 1.5% | 1.25% |
| 3. ESS | 3.0% | — |
| 4. LAPB | — | 2.5% |
| Wt. ratio of SCG:SCI | 1:1 | 1:1 |
| Wt. ratio of (SCG + SCI):ESS (or LAPB) | 1:1 | 1:1 |
| pH (as such) | 5.5 | 5.5 |
| Appearance @ 25° C. | Opaque | Opaque |

Comparative Examples 21A to 26A

These comparative examples shows that SCG alone, or in combination with SCI, and GI alone do not remain isotropic at skin pH (5.0 to 6.0). All compositions are prepared in water.

| Aqueous cleansing composition | Ex. 21A | Ex. 22A | Ex. 23A | Ex. 24A | Ex. 25A | Ex. 26A |
|---|---|---|---|---|---|---|
| 1. SCG | 5.0% | 5.0% | 7.0% | 7.0% | — | — |
| 2. SCI | — | — | 5.0% | 5.0% | — | — |
| 3. GI | — | — | — | — | 10.0% | 7.5% |
| a. SCG in GI | — | — | — | — | 5.0% | 5.0% |
| b. SCI in GI | — | — | — | — | 5.0% | 2.5% |
| Wt. ratio of SCG:SCI (in GI) | — | — | — | — | 1:1 | 2:1 |
| Wt. ratio of SCG:SCI | 1:0 | 1:0 | 3:2 | 3:2 | — | — |
| pH (as such) | 5.5 | 6.0 | 5.5 | 6.0 | 5.5 | 6.0 |
| Appearance @ 25° C. | Opaque | Opaque | Opaque | Opaque | Opaque | Opaque |

Comparative Example 27A to 30A

This example consists of the same three surfactants and same pH as claimed in Jawale et al. (US Pub. No. 2013/0189212). It is noted that if SCG is used as a primary surfactant i.e. if the quantity of SCG is increased equal to or more than SCI than it results in opaque compositions. All the surfactants are mixed in their individual physical forms as per the teachings of Jawale et. al.

| Aqueous cleansing system | Ex. 27A | Ex. 28A | Ex. 29A | Ex. 30A |
|---|---|---|---|---|
| 1. SCG | 1.25% | 5.00% | 6.25% | 6.81% |
| 2. SCI | 1.25% | 2.50% | 1.25% | 0.68% |
| 3. Cocobetaine | 2.5% | 7.50% | 7.50% | 7.50% |
| Wt. ratio of SCG:SCI | 1:1 | 2:1 | 5:1 | 10:1 |
| Wt. ratio of (SCG + SCI):Cocobetaine | 1:1 | 1:1 | 1:1 | 1:1 |
| pH (as such) | 5.5 | 6.0 | 6.0 | 6.0 |
| Appearance @ 25° C. | Opaque | Opaque | Opaque | Opaque |

Example B

Moisturization Effect of the Inventive Aqueous Cleansing Composition

The moisturization effect of the inventive aqueous cleansing composition of the present invention was suitably determined by its moisture retention capability on hair which was measured through Thermo Gravimetric Analysis (TGA). Three different compositions as given in the below table were prepared and taken for the study.

| Formulation No. | Composition | % active | Ratio of SCG:SCI:Milcoside 100 |
|---|---|---|---|
| 1 | Base composition | 12 | — |
| 2 | Inventive Aqueous composition (of Example 3) | 12 | (2:1):1 |

-continued

| Formulation No. | Composition | % active | Ratio of SCG:SCI:Milcoside 100 |
|---|---|---|---|
| 3 | SCG + SCI + Milcoside 100 (mixed in their individual physical forms) | 12 | (2:1):1 |

Base Composition:

Base composition is a standard composition which does not contain the active surfactants i.e. N-acyl glycinates and O-acyl isethionates. Below given is the base composition used in the present invention.

| Sr. No. | Ingredients | % w/w |
|---|---|---|
| 1 | Sodium lauryl ether sulfate | 40.00 |
| 3 | Cocomono ethanolamide | 2.00 |
| 4 | Preservative | 0.70 |
| 5 | EDTA | 0.10 |
| 6 | Distilled Water | q.s. to 100 |

The moisture retention capability of the inventive aqueous cleansing composition i.e. Formulation No. 2 was compared with Formulation No. 1 (Base composition) and Formulation No. 3 (Composition prepared by mixing the same surfactants in same ratio in their individual physical forms)

Procedure: Following procedure was followed to measure the moisture retention.

1. 200 ml of 10% solution of Formulation No. 1 (Base composition) was prepared.
2. Dried and weighed hair swatches (Indian virgin hair) were labeled with respective sample names and taken for study.
3. Hair swatches were dipped into the solutions and held with clips. The hair swatches were kept for 1 hour in the same condition.
4. After 1 hour, all the swatches were removed and the excess solution or water was dripped out by means of filter paper (Do not wipe out excessively or roughly as hair loss may occur).
5. The swatches were then dried at temperature of around 25-27° C. and RH 55-60%.
6. The % weight loss of hair moisture is determined by Thermo Gravimetric Analysis (TGA). The TGA measurements were conducted using the Perkin Elmer Instrument for moisture determination in hair samples.

Conditions:

Measuring Cell—Perkin Elmer

Weighing PAN—Alumina 40 ul

Sample Preparation—As such treated and dried hair samples (10 to 11 mg) were exposed to heat and continuous measurements were recorded automatically. All measurements were recorded while heating the samples from 30 to 300° C. at the rate of 10° C. per minute. The moisture content was measured at every 10 deg C.

Atmosphere—Nitrogen 20 cm3/minute. The calibration of the instrument was done using Indium as a standard.

The % weight loss was determined by the below mentioned formula:

% weight loss of moisture={Initial weight−final weight (at specific Temp)}/Initial weight*100

Figure 5:
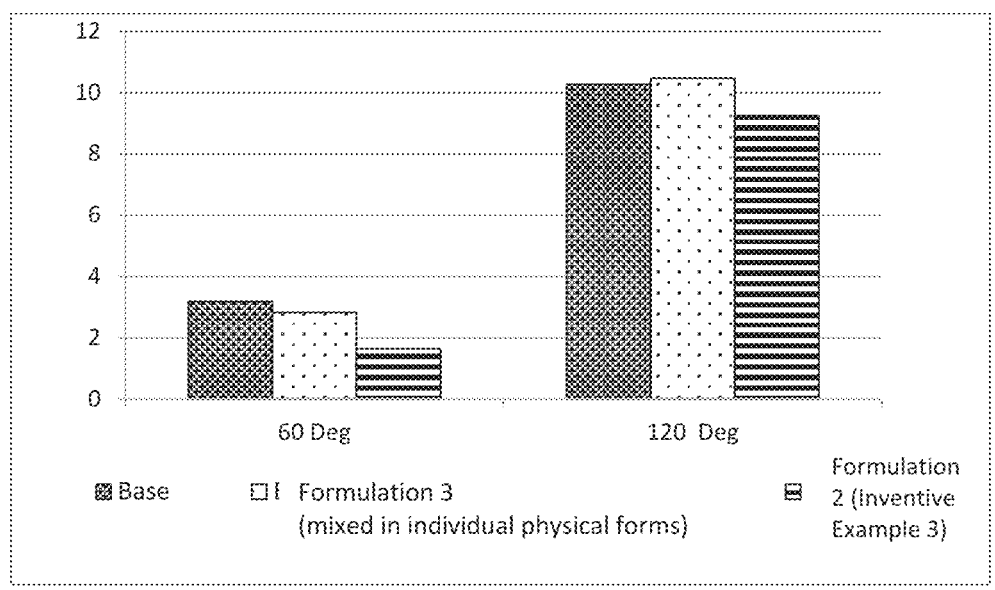
FIG. 5 shows a bar graph illustrating % weight loss of moisture for various formulations.

From the graphs shown in FIG. 5 is evident that the Formulation No. 2 (inventive surfactant composition of Example 3) prevents the loss of moisture from skin and hair and delivers the improved moisturizing benefits as compared to Formulation No. 1 (Base) and Formulation No. 3 (mixed in their individual physical forms).

Example C

Foaming

The foam volume and lather potential of the inventive cleansing compositions are substantially higher than the individual surfactants. This synergistic foaming and lather potential of the invention compositions were measured and compared with individual surfactants as below.

Foam Volume:

Foam volume was measured as per the below procedure.

100 mL of 1% aqueous solution of SCI (aqueous solution of SCI is prepared by heating the SCI at 80° C. in water having hardness of 150 ppm) was used to evaluate the foam volume.

The SCI surfactant solution was taken in a kitchen blender and mixed at a speed of 2700 rpm for 60 sec.

Foam generated was then collected in the 1000 mL measuring cylinder and the foam volume was measured.

Similarly the above procedure is repeated for SCG, CAPSB and the inventive composition of Example 7 (no heating is required for these surfactants/inventive composition as given above for SCI). The pH of all surfactants solutions were maintained at pH 7. The foam volumes of all surfactants were compared graphically.

Figure 6:
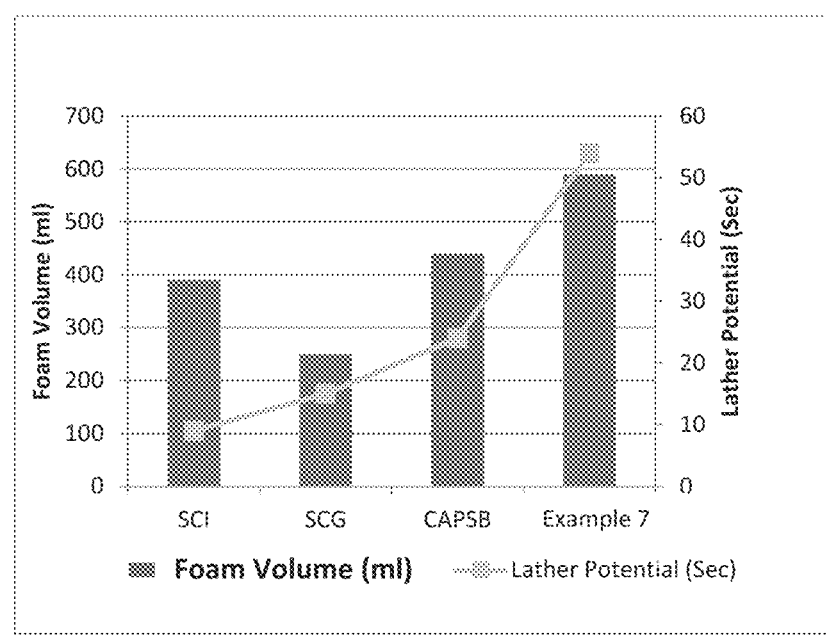
FIG. 6 shows a bar graph illustrating the foam volume and lather potential of various surfactants with Example 7.

As evident in the graph in FIG. 6, Inventive composition of Example 7 exhibits significantly high foam volume than the individual surfactants i.e. SCI, SCG, and CAPSB.

Lather Potential:

Lather potential was measured as per the below procedure.

200 mL of 1% aqueous solution of SCI (aqueous solution of SCI is prepared by heating the SCI at 80° C. in water having hardness of 150 ppm) was used to evaluate the lather potential (secs).

The surfactant was taken in a kitchen blender and mixed at a speed of 2700 rpm for 60 sec.

The foam generated in the kitchen blender was immediately poured through the Lather Potential Assembly (as explained below).

The pouring was carried for exactly 15 sec, and waited till the wire was visible. The time from pouring of foam into the funnel until the appearance of the wire reference point, is called lather drainage time or lather potential and is recorded in sec.

Lather Potential Assembly: It consists of a plastic beaker having sieve kept on its mouth. The outer diameter of plastic beaker shall be the same as that of sieve. A funnel is adjusted with the help of a clamp such that its stem bottom rests on the sieve.

The above procedure was repeated for SCG, CAPSB, and the inventive composition of Example 7 (no heating is required for these surfactants/inventive composition as given above for SCI). The pH of all surfactants solutions were maintained at pH 7. The lather potential (secs) of all surfactants were compared graphically as mentioned above. As evident in the above graph, inventive composition Example 7 exhibits significantly high lather potential than the individual surfactants i.e. SCI, SCG, and CAPSB.

Similarly, below is the foam volume and lather potential of the inventive composition Example 4.

Figure 7:
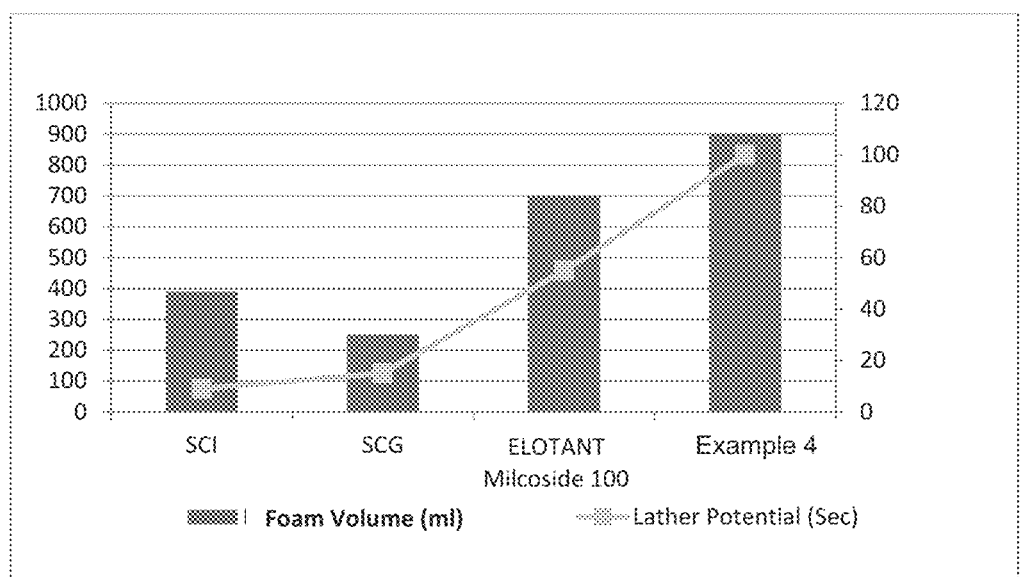
FIG. 7 shows a bar graph illustrating the foam volume and lather potential of various surfactants with Example 4.

As evident in the graph in FIG. 7, inventive composition Example 4 exhibits significantly high lather potential than the individual surfactants i.e. SCI, SCG, and ELOTANT Milcoside 100.

Example D

Sensory Test

The inventive aqueous cleansing composition also provides a very good sensory feel to the skin. The final personal care/cleaning formulation (Example D1) containing the invention aqueous composition (of Example 4) was prepared for this sensory test. FIGS. 1, 2 and 3 illustrates the results of the sensory test conducted at different time period of the test and is compared with the commercially available market body wash samples.

Example D1

Body Wash

| Ingredients | % (w/w) |
|---|---|
| Phase A | |
| Deionized water | To make 100.0 |
| Glycerin | 05.00 |
| Phase B | |
| Inventive cleansing composition (Example 4) | 52.00 |
| Phase C | |
| Ethylene Glycol Di Stearate | 02.00 |
| PEG 150 Di Stearate | 02.00 |
| Phase D | |
| Polyquaternium - 7 | 02.00 |
| Hydrolyzed Wheat Protein | 02.00 |
| EDTA disodium salt | 00.10 |
| Phenoxyethanol with Parabens | 00.50 |

Procedure to prepare Body wash: All the ingredients of phase A and phase B were mixed until homogenous and the mixture is heated upto 70° C. Ingredients of phase C were added and stirred until uniform mixture is obtained. The mixture was then cooled to room temperature and ingredients of phase D were added with homogenous mixing. The pH of the final formulation was adjusted to pH 5.5 with 50% citric acid.

Procedure for Sensory Evaluation:

The above prepared body wash (containing composition of example 4) is compared with standard Benchmark body wash formulation having skin moisturization as one of the standard claim. Both the body washes were given to the expert panel members (n=15) for home usage test to evaluate the comparative sensory of both the body washes during actual bathing. Panels rated on the scale of 1-10 both the body wash for the sensory properties. Scale 1 is the lowest and scale 10 represents the highest performance. Results are shown in FIGS. 1, 2 and 3.

As evident in FIG. 1, FIG. 2, and FIG. 3 in the drawings, the inventive composition of Example 4 is comparable in sensorial properties to the Market body wash.

Example E

The novel aqueous cleansing compositions of the present invention can be blended with other desired ingredients to prepare the final personal care/cleansing formulations. Below are the examples of such formulations.

Example E1

Sulfate Free Shampoo

| Ingredients | % (w/w) |
|---|---|
| Phase A: | |
| Deionized water | q.s to make 100 |
| Polyquaternium 10 (UCARE Polymer JR-400) | 00.20 |
| Phase B: | |
| Inventive cleansing composition (Example 3) | 50.00 |
| Phase C: | |
| PEG-120 Methyl Glucose Trioleate (and) Propanediol (Glucamate™ VLT) | 2.00 |
| Phase D: | |
| Amodimethicone (Dow Corning® 8500) | 0.50 |
| Polyquaternium 7 (Galsilk 7) | 2.00 |
| EDTA disodium salt | 0.10 |
| Preservative blend of Phenoxyethanol, Undecylenoyl Glycine, and Capryloyl Glycine (Galguard Trident) | 0.50 |

Procedure: Polyquaternium 10 is dispersed in water and all the ingredients of phase A and phase B were mixed to prepare homogeneous mixture. Phase C ingredients were added to the above mixture and mixed well. Phase D ingredients were added and mixed well to form homogeneous mass. The pH of the final formulation was adjusted to 5.5 with 50% citric acid. Fragrance and color is added as per the requirement.

Example E2

Crystal Clear Shower Gel

| Ingredients | % (w/w) |
|---|---|
| Phase A | |
| Deionized water | q.s. to make 100 |
| Glycerine | 15.00 |
| Phase B | |
| Sodium Lauryl Ether Sulfate (Galaxy LES, 28%) | 12.00 |
| Inventive cleansing composition (Example 4) | 40.00 |
| Phase C | |
| Isostearamide MIPA and Glyceryl Laurate (ANTIL® SPA 80) | 2.00 |
| Phase D | |
| Polyquaternium 7 (Galsilk 7) | 2.00 |
| Hydrolyzed Wheat Protein | 1.00 |
| EDTA disodium salt | 0.10 |
| Preservative blend of Phenoxyethanol, Undecylenoyl Glycine, and Capryloyl Glycine (Galguard Trident) | 0.50 |

Procedure: Mix all the ingredients of phase A and phase B and mixed well to form homogenous mixture. Phase C ingredients are added to the above mixture and mixed well. Phase D ingredients are added and mixed well to form homogeneous mass. If required the pH of the final formulation is adjusted to 6.2 with 50% citric acid. Fragrance and color were added as per the requirement.

Example E3

Mild Face Wash

| Ingredients | % (w/w) |
|---|---|
| Phase A | |
| Deionized water | q.s. to make 100 |
| Hydroxy Ethyl Cellulose | 0.30 |
| Glycerin | 10.00 |
| Phase B | |
| Inventive cleansing composition (Example 5) | 25.00 |
| Phase C | |
| PEG 150 Distearate | 1.5 |
| Phase D | |
| Hydrolyzed Barla Protein | 1.00 |
| Panthequat | 0.50 |
| EDTA disodium salt | 0.10 |
| Preservative blend of Phenoxyethanol, Undecylenoyl Glycine, and Capryloyl Glycine (Galguard Trident) | 0.50 |

Procedure: Hydroxy Ethyl Cellulose was dispersed in water. All the ingredients of phase A and phase B were added and heated to 75° C. with slow stirring. Phase C ingredients were then added and mixed to form homogenous mixture. The mixture was cooled to room temperature and added phase D, stirred until uniform. The pH of the final formulation was adjusted to 5.8 with 50% citric acid. Fragrance and color were added as per the requirement.

This invention may be embodied in other forms or carried out in other ways without departing from the spirit or essential characteristics thereof. The embodiments given hereinbefore are therefore to be considered as in all respects illustrative and not restrictive, the scope of the invention being indicated by the appended claims, and all changes which come within the meaning and range of equivalency are intended to be embraced therein. It is to be understood that no limitation with respect to the specific embodiments illustrated is intended or should be inferred.

The invention claimed is:

1. An isotropic, flowable, aqueous cleansing composition comprising:
    an aqueous blend of N-acyl glycinates of Formula I, and O-acyl isethionates of Formula II;

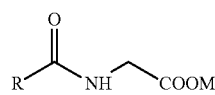

Formula I

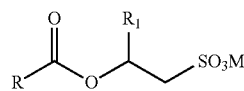

Formula II wherein,
R is selected from $C_5$ to $C_{22}$ alkyl group, saturated or unsaturated,
$R_1$ is selected from H or methyl, and
M is a cation selected from $Li^+$, $Na^+$, $K^+$, $NH_4^+$ or a quaternary ammonium cation derived from tertiary amines;
prepared by the process comprising
A) reacting more than one equivalent of fatty acid chloride with alkali metal or ammonium salts of hydroxyalkyl sulphonates to obtain compounds of Formula II, and
B) reacting unreacted fatty acid chloride in the product of step (A) with glycine in the presence of a base under aqueous Schotten Baumann reaction conditions to yield compounds of Formula I;
the weight ratio of N-acyl glycinates of Formula I to O-acyl isethionates of Formula II is in range of 1.0:1.0 to 10.0:1.0, and
a solubilizing surfactant
wherein the weight ratio of the aqueous blend of N-acyl glycinates of Formula I, and O-acyl isethionates of Formula II: the solubilizing surfactant is from 1.0:0.1 to 1.0:1.0,
and the pH of the aqueous cleansing composition is 5.0 to 6.0.

2. An isotropic, flowable, aqueous cleansing composition comprising:
    an aqueous blend of N-acyl glycinates of Formula I, and O-acyl isethionates of Formula II;

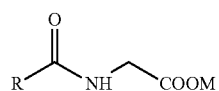

Formula I

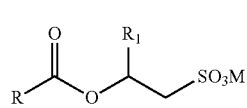

Formula II wherein,
R is selected from $C_5$ to $C_{22}$ alkyl group, saturated or unsaturated,
$R_1$ is selected from H or methyl,
M is a cation selected from $Li^+$, $Na^+$, $K^+$, $NH_4^+$ or a quaternary ammonium cation derived from tertiary amines,
the weight ratio of Formula I to Formula II is from 1.0:1.0 to 10.0:1.0, and
a solubilizing surfactant
wherein the weight ratio of the aqueous blend of N-acyl glycinates of Formula I, and O-acyl isethionates of Formula II: the solubilizing surfactant is from 1.0:0.1 to 1.0:1.0,
and the pH of the aqueous cleansing composition is 5.0 to 6.0.

3. The solubilizing surfactant as claimed in claim 1 is selected from a group consisting of alkyl amidopropyl sulfobetaines, alkyl polyglucosides, sulfosuccinates, alkyl betaines, alkyl amidopropyl betaines, and alkyl ether sulfates and any combinations thereof.

4. The aqueous cleansing composition of claim 1, wherein the composition is isotropic and flowable at temperature of 25° C.

5. The aqueous cleansing composition of claim 1, wherein the viscosity of the aqueous cleansing composition is between 500-10,000 cps.

6. The aqueous cleansing composition of claim 1, wherein the aqueous cleansing composition has total solids content of 1.0 to 50.0% by weight.

7. An isotropic personal care formulation comprising 1.0 to 20.0% of the aqueous cleansing composition as claimed in claim 1.

8. The isotropic personal care formulation as claimed in claim 7 selected from the group consisting of shampoos, hand soaps, body washes, face washes, hand washes, shower gels, and baby bubble bath and any combination thereof.

9. The aqueous cleansing composition as claimed in claim 1 wherein the composition is spray dried to get a solid form.

* * * * *